United States Patent [19]

Hughes

[11] Patent Number: 4,635,857
[45] Date of Patent: Jan. 13, 1987

[54] ATOMIZING APPARATUS

[75] Inventor: Nathaniel Hughes, Palm Springs, Calif.

[73] Assignee: Vortran Corporation, Culver City, Calif.

[21] Appl. No.: 555,703

[22] Filed: Nov. 28, 1983

Related U.S. Application Data

[63] Continuation-in-part of Ser. No. 213,843, Dec. 8, 1980, Pat. No. 4,453,542.

[51] Int. Cl.⁴ .................... B05B 5/02; A61M 11/02
[52] U.S. Cl. ........................ 239/690; 128/200.18; 128/200.21; 128/203.27; 239/135; 239/338; 239/370; 239/590.3; 261/DIG. 65; 261/78.2
[58] Field of Search ............... 239/102, 132, 133, 135, 239/338, 370, 590, 590.3, 590.5, 690, DIG. 20, DIG. 23; 128/200.14, 200.18, 200.21, 203.27; 261/78 A, DIG. 65

[56] References Cited

U.S. PATENT DOCUMENTS

| | | | |
|---|---|---|---|
| 3,652,015 | 3/1972 | Beall | 239/338 |
| 4,241,877 | 12/1980 | Hughes | 239/590.3 |
| 4,267,974 | 5/1981 | Kienholz et al. | 128/200.18 |
| 4,301,970 | 11/1981 | Craighero | 239/338 |
| 4,376,514 | 3/1983 | Coffee | 239/690 |
| 4,453,542 | 6/1984 | Hughes | 239/338 |
| 4,461,425 | 7/1984 | Miller | 128/203.27 |

Primary Examiner—Joseph F. Peters, Jr.
Assistant Examiner—Michael J. Forman
Attorney, Agent, or Firm—Christie, Parker & Hale

[57] ABSTRACT

A perforated planar member is spaced from the outlet of a vortex generating transducer and a tube is coupled between the outlet of the transducer and the perforated member to completely close the space therebetween. Preferably, the perforated member is a screen composed of non-conductive criss-crossing wires having resonant dimensions as to a component frequency of the sonic waves generated by the transducer. In addition, the screen is also preferably spaced from the outlet of the transducer a resonant distance as to the component frequency. A drag member is spaced from the perforated member. Preferably, the drag member is cylindrical and its axis lies transverse to the plane of the perforated member; the drag member is spaced from the perforated member a resonant distance as to a component frequency of the sonic waves generated by the transducer. Atomization in the described apparatus is enhanced by means of thermal and/or electrical energy.

15 Claims, 6 Drawing Figures

Fig. 1

- SOURCE OF AIR UNDER PRESSURE
- SOURCE OF LIQUID TO BE ATOMIZED
- VORTEX GENERATING TRANSDUCER
- SPIN CHAMBER
- RESONANT SCREEN
- DRAG BAR
- SOURCE OF ELECTRICAL ENERGY
- SOURCE OF THERMAL ENERGY

Fig. 6

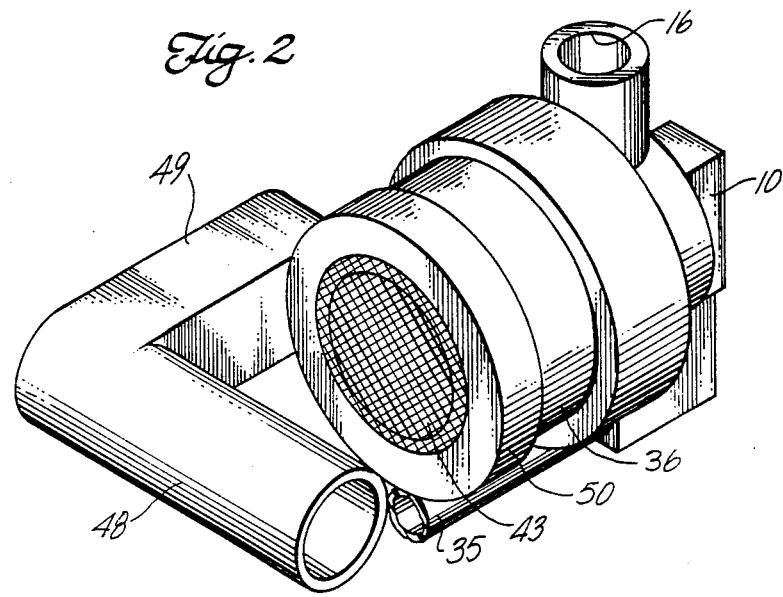
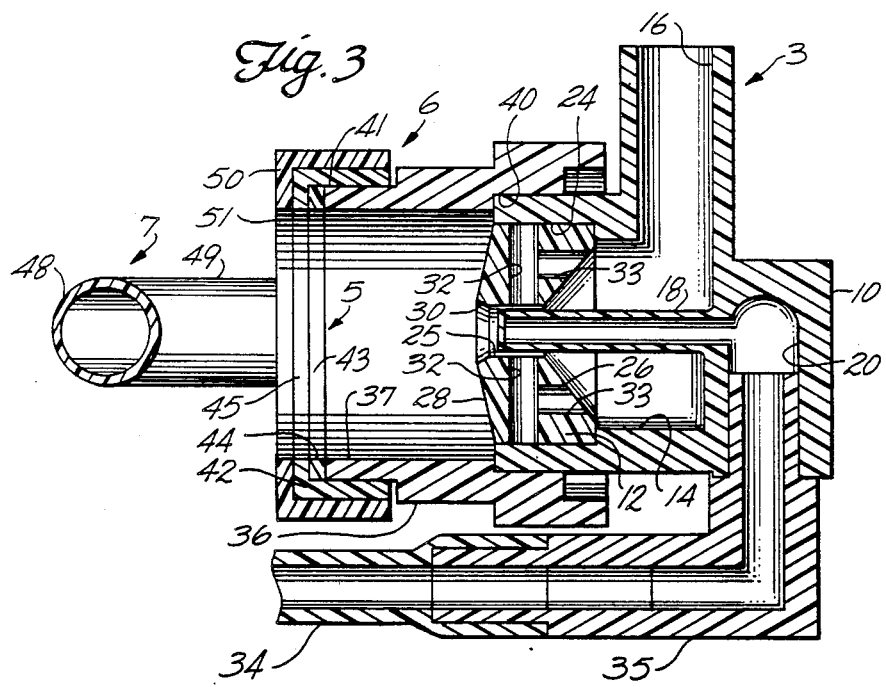

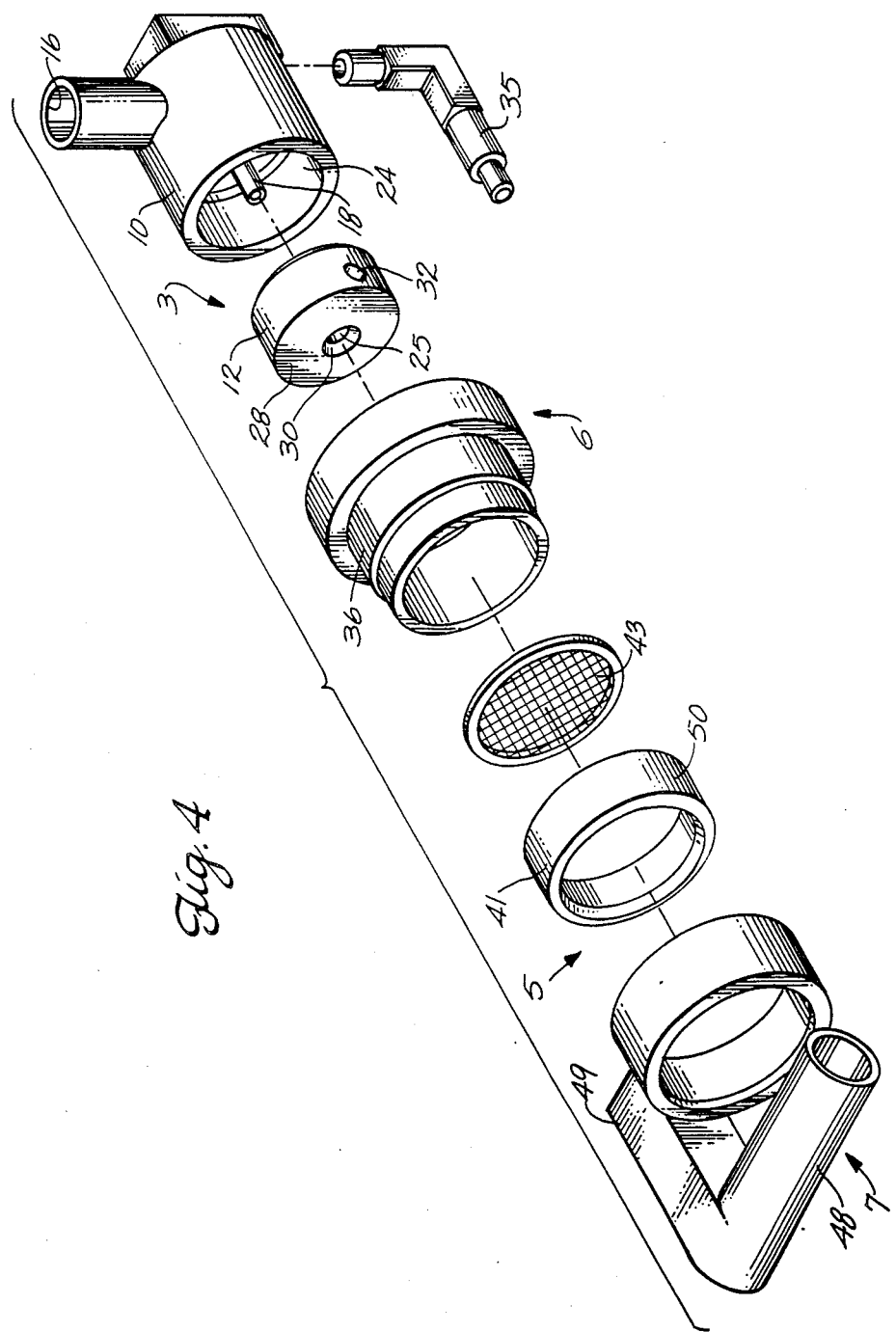

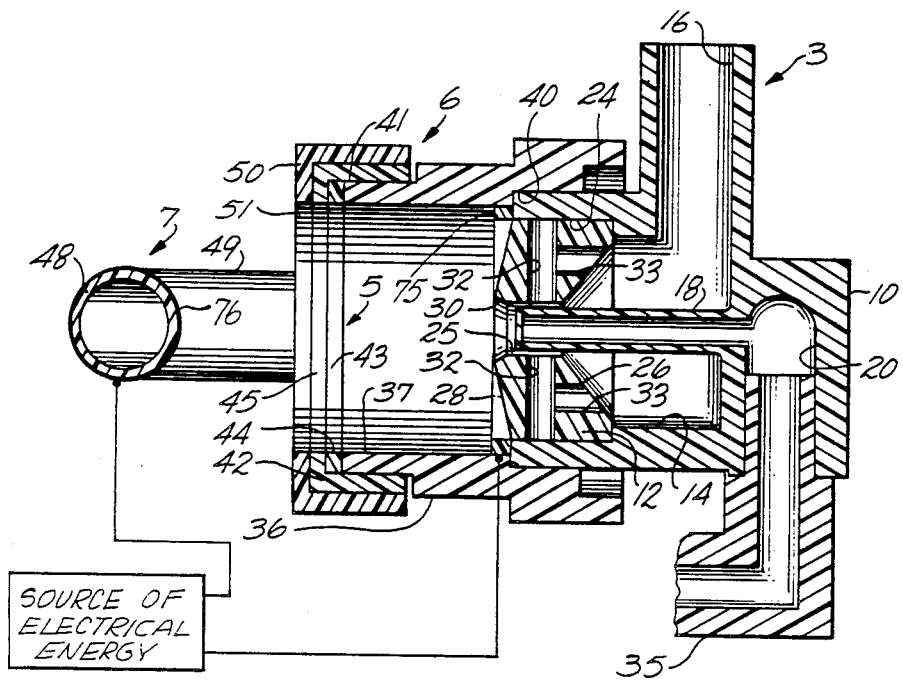

ATOMIZING APPARATUS

CROSS REFERENCE TO RELATED APPLICATIONS

This application is a continuation-in-part of application Ser. No. 213,843, filed Dec. 8, 1980, now U.S. Pat. No. 4,453,542, issued June 12, 1984.

BACKGROUND OF THE INVENTION

This invention relates to fluid handling and, more particularly, to apparatus for finely atomizing liquid by a means of pressurized gas.

My U.S. Pat. Nos. 4,109,862, 4,189,101, 4,241,877 and 4,453,542 (pending application Ser. No. 213,843, filed Dec. 8, 1980) incorporated herein by reference, disclose various embodiments of a vortex generating transducer. A flow passage has a cylindrical upstream section and a cylindrical outlet restriction aligned with a flow axis. A hollow rod aligned with the flow extends completely through the upstream section to the restriction where it opens into the passage. An inlet aligned with an inlet axis at an angle to the flow axis opens into the upstream section. A source of gas under pressure is connected to the inlet and a source of liquid to be atomized is connected to the interior of the rod. The described transducer generates gas vortices that atomize the liquid as it leaves the end of the rod at the restriction. In one very effective embodiment, auxiliary flow passages are connected between the upstream section and the restriction, preferably opening into the restriction in a radial direction toward the flow axis to focus the vortex energy. A sub-atmospheric pressure, which facilitates atomization, is produced by the vortex action in the vicinity of the outlet.

SUMMARY OF THE INVENTION

According to a feature of the invention, a perforated planar member is spaced from the outlet of a vortex generating transducer and a tube is coupled between the outlet of the transducer and the perforated member to completely close the space therebetween. Preferably the perforated member is a screen composed of nonconductive criss-crossing wires having resonant dimensions as to a component frequency of the sonic waves generated by the transducer. In addition, the screen is also preferably spaced from the outlet of the transducer a resonant distance as to the component frequency. As a result, substantially more of the energy of the pressurized gas applied to the transducer is utilized to atomize liquid supplied to the transducer. A drag member is spaced from the perforated member. Preferably, the drag member is cylindrical and its axis lies parallel to the plane of the perforated member; the drag member is spaced from the perforated member a resonant distance as to a component frequency of the sonic waves generated by the transducer Another feature of the invention is the enhancement of the atomization in the described apparatus by means of thermal and/or electrical energy.

BRIEF DESCRIPTION OF THE DRAWINGS

The features of specific embodiments of the best mode contemplated of carrying out the invention are illustrated in the drawings, in which:

FIG. 1 is a schematic block diagram of the apparatus incorporating the features of the invention;

FIG. 2 is a perspective view of an embodiment of the apparatus of FIG. 1;

FIG. 3 is a side sectional view of the apparatus of FIG. 2;

FIG. 4 is an exploded perspective view of the apparatus of FIG. 2;

FIG. 5 is a side sectional view of another embodiment of the apparatus of FIG. 1 with connections to a source of electrical energy; and FIG. 6 is a side sectional view of a nebulizer incorporating the apparatus of FIG. 1 and a source of thermal energy.

DETAILED DESCRIPTION OF THE SPECIFIC EMBODIMENTS

In FIG. 1, a source 2 of of air under pressure is fluidically connected to a gas inlet of a vortex generating transducer 3 and a source 4 of liquid to be atomized is fluidically connected to a liquid inlet of vortex generating transducer 3. Vortex generating transducer 3 has an outlet from which atomized liquid and air emanate. A resonant perforated planar member 5 is spaced from the outlet of vortex generating transducer 3 and a tubular spin chamber 6 is coupled between the outlet of vortex generating transducer 3 and resonant member 5. A drag bar 7 is spaced from resonant member 5. An optional source of electrical energy 8 and/or source of thermal energy is coupled to the described apparatus in the vicinity of drag bar 7.

Reference are made to FIGS. 2, 3 and 4 for a detailed description of the apparatus of FIG. 1. Vortex generating transducer 3 comprises a body member 10 and an insert 12, which are preferably injection-molded parts. A large cylindrical bore 14 and a small cylindrical bore 16, which opens into bore 14, are formed in body member 10. Bores 14 and 16 lie on intersecting orthogonal axes. Body member 10 includes a hollow, cylindrical rod 18 that extends the length of bore 14 in axial alignment therewith. A small cylindrical bore 20 is formed in body member 10 behind rod 18. Bores 16 and 20 lie on parallel axes. A bore 22 extends through rod 18 from bore 20 to the exterior end of bore 14.

A counterbore 24 is formed in bore 14 at its exterior end. Insert 12 fits into counterbore 24, where it is cemented in place. A cylindrical bore 25, which has a slightly larger diameter than rod 18, is formed in insert 12. Rod 18 extends through bore 25 in axial alignment therewith to form therebetween a small annular passage. The open end of bore 22 is preferably recessed slightly from the exit end of bore 25. The interior end of insert 12 has a conical concavity 26 and the exterior end thereof has a spherical convexity 28. A conical concavity 30 is formed between the center of convexity 28 and bore 25.

Oppositely disposed radial bores 32 extend through insert 12 from its periphery to bore 25. A pair of oppositely disposed axial bores 33 extend through insert 12 from concavity 26 to bores 32, thereby forming with bores 32 a pair of auxiliary passages. Liquid source 4 (FIG. 1) is connected by a hose 34 and a coupling tube 35 to bore 20, which serves as the liquid inlet of transducer 3. Bore 16 serves as a gas inlet. Bore 14 serves as an upstream section of a flow passage while bore 25 serves as a restriction in the flow passage. Concavity 30 serves as the outlet of vortex generating transducer 3. Bores 14 and 25 and concavity 30 all are aligned with a flow axis. The gas inlet is aligned with an inlet axis that intersects the flow axis at a right angle.

Spin chamber 6 is a tubular member 36 having a cylindrical inner surface 37 aligned with the flow axis of vortex generating transducer 3. At one end, member 36 has on its inner surface a recess 40 adapted to receive the outer surface of body member 10, where insert 12 fits therein. At the other end, the outer surface of member 36 has a recess 41 that receives the inner surface of a tubular end cap 42. End cap 42 has a circular end opening 45 with the same diameter as surface 37. Resonant member 5 is a circular screen. The edges of screen 43 are secured to an annular frame 44, which is clamped between the end of member 36 and end cap 42. The inside diameter of frame 44 has the same diameter as surface 37. Screen 43 is made of criss-crossing, preferably nylon, wires each having a circular cross section. Screen 43 is spaced from the outlet of vortex generating transducer 3 and spin chamber is coupled between the outlet of transducer 3 and screen 43 to completely close the space therebetween.

Drag bar 7 has in a one-piece construction a cylindrical drag member 48 connected by a support arm 49 to a cap 50 that fits over end cap 42 and is so mounted on spin chamber 6 that the cylindrical axis of drag member 48 lies at a right angle to the flow axis directly in front of screen 43. Cap 50 has a circular opening with the same diameter as surface 37.

Typically, body member 10, insert 12, tubular member 36, end cap 42, ring 44 and drag bar 7 are all injection molded plastic parts bonded together by an appropriate adhesive.

Typical dimensions for the described apparatus are as follows:

| | |
|---|---|
| Length of bore 14 | .205 inch |
| Diameter of bore 14 | .312 inch |
| Length of rod 18 | .372 inch |
| Diameter of rod 18 | .066 inch |
| Diameter of bore 22 | .054 inch |
| Diameter of bore 16 | .125 inch |
| Diameter of bore 25 | .730 inch |
| Length of bore 25 | .730 inch |
| Included angle of concavity 26 | 60 degrees |
| Included angle of concavity 30 | 45 degrees |
| Radius of convexity 28 | .125 inch |
| Base diameter of concavity 26 | .312 inch |
| Base diameter of concavity 30 | .130 inch |
| The space between the end of rod 18 and the end of bore 25 | .005 inch |
| Diameter of bores 33 | .050 inch |
| Diameter of bores 32 | .060 inch |
| Diameter of surface 37 | .409 inch |
| Diameter of opening 45 | .409 inch |
| Inside diameter of ring 44 | .409 inch |
| Diameter of opening 51 | .409 inch |
| Center-to-center spacing of wires of screen 43 | .025 inch |
| Diameter of wires of screen 43 | .004 inch |
| Distance from insert 12 to screen 43 | .276 inch |
| Distance from screen 43 to the edge of rod 48 | .200 inch |
| Outside diameter of rod 48 | .250 inch |

For a description of the operation of vortex generating transducer, reference is made to my U.S. Pat. Nos. 4,109,862, 4,189,101, 4,241,877, 4,240,293, 4,372,169 and 4,453,542 (application Ser. No. 213,843, filed Dec. 8, 1980), the disclosures of which are incorporated fully herein by reference. For apparatus having the above dimensions, typical pressure for source 2 is between 4 and 20 psig. Briefly, air or other gas introduced into transducer 3 through gas inlet 16 forms rapidly spinning vortices in the upstream section of the flow passage. The vortically flowing gas travels through the restriction formed by bore 25 and rod 18 and through the auxiliary passage so as to converge near the open end of rod 18 where the rapidly moving gas meets liquid supplied through rod 18. The gas thus entrains and atomizes the liquid to form liquid particles in the gas of the order of 1-10 microns. At the outlet of transducer 3 is produced a sub-atmospheric pressure that draws liquid through rod 18 and causes cavitation in this liquid as it emanates from the end of rod 18. Thus, the liquid source 4 can be at atmospheric pressure, if desired. Liquid atomization is enhanced by a supersonic process taking place in transducer 3. As a result, shock waves are formed as the gas exits transducer 3 and sonic energy in addition to vortex energy is present in spin chamber 6.

At very low flow velocities, i.e., Reynolds numbers, the drag coefficient and thus the drag forces increase rapidly. At such low Reynolds numbers, viscosity is a predominant parameter in determining drag and viscosity effects dominate over gravitational effects.

Member 48 presents drag to and induces vortex action in the gas and liquid leaving member 5. Screen 43 serves to slow the velocity of the moving gas and thus increases the drag effect of member 48 thereon. As a result, member 48 exerts more drag force on the gas and atomized liquid, creating vortical action and pulsating, dancing fluid activity on the surface of member 48 facing towards screen 43. It has been found that the effectiveness of member 48 in atomizing the liquid depends upon the distance between member 48 and screen 43. For this reason, it is believed that member 48 also serves to cause resonance of one or more components of the sonic energy impinging thereon. Thus, the spacing between screen 43 and member 48 is emperically selected to cause resonance of one or more components of the sonic waves generated by transducer 3. The liquid particles emanating from the apparatus in the region of bar 48 are of the order of 1 or 2 microns.

In summary, the described apparatus processes the gas and liquid to be atomized in three stages. In the first stage, a high velocity stream of vortices and sonic waves is produced. In the second stage, velocity of the stream is reduced to an intermediate value and the sonic waves are enhanced by resonance. In the third stage, the sonic waves are further enhanced by resonance, the velocity of the stream is reduced to a creeping motion, and futher vortex action takes place. As a result, the energy of the gas from the source is effectively utilized to finely atomize the liquid.

It has been observed that a large electric field is produced in the described apparatus by virtue of ionization of the gas. Ionization can be enhanced by application of electrical energy to the apparatus, as represented by block 8 in FIG. 1. As shown in FIG. 5, an electrically conductive ring 75 is secured to the end of body member 10 around bore 24 and an electrically conductive layer 76 is deposited on the outer surface of member 48. The output terminals of source 8 are connected by lead wires 77 and 78, respectively, to ring 75 and layer 76 (by lead wires 77 and 78, respectively). Lead wire 77 could pass through member 36 as shown. Lead wire 78 could pass through arm 49 to the edge of cap 50 and through cap 50 the exterior of the apparatus. Source 8 could be alternating current or direct current. If source 8 is alternating current, its frequency could be synchronized to that of one of the components of the sonic waves.

In addition to or instead of electrical energy, atomization can also be enhanced by application of thermal energy or both to the apparatus as represented by block 9 in FIG. 1. In FIG. 6, the apparatus illustrated in FIGS. 2 through 4, which is represented by reference numeral 79, is incorporated in a medical nebulizer with source 9. A liquid 80 to be atomized such as water or medication is stored in a bottle 81 having an exit opening 82 at its top. A fitting 83 extends through the wall of bottle 81. Source 2 is connected by fitting 83 to the gas inlet of apparatus 79. Liquid 80 is connected by a tube 84 to the liquid inlet of apparatus 79. Source 9 takes the form of a heater plate 85 having an electrical connector 86 outside bottle 81. A source of electrical power 87 such as, for example standard 110 volt 60-cycle power, is supplied to connector 86. The atomized liquid emanating from apparatus 79 is heated by plate 85. Much of the heated liquid returns to liquid 80 stored at the bottom of bottle 81. As a result, the temperature of the liquid fed to device 79 rises and more effective atomization takes place. Heater 85 also serves to introduce thermal energy into the atomized air liquid mist leaving exit opening 82. The added thermal energy further slows down the velocity of the air and thus accentuates the drag forces. In effect, it increases the vortical action of the gas and thereby its atomizing potential. An alternative way to introduce thermal energy into the described process is to provide a heater in member 48.

A noteworthy characteristic of the described apparatus is the cooling effect it has on the air liquid mist. The cooling effect appears to increase with temperature. Thus, the described apparatus has potential application as a heat exchanger and for refrigeration.

The described embodiments of the invention are only considered to be preferred and illustrative of the inventive concept; the scope of the invention is not to be restricted to such embodiments. Various and numerous other arrangements may be devised by one skilled in the art without departing from the spirit and scope of the invention. Although embodiments of the invention having specified dimensions have been disclosed, the devices may be scaled up or down in size without a loss in effectiveness.

What is claimed is:

1. Atomizing apparatus comprising:

vortex generating transducer means for at least partially atomizing a fluid and having a gas inlet and an outlet;

a perforated planar member spaced from the outlet of the transducer means;

a tube coupled between the outlet of the transducer means and the perforated member completely closing the space therebetween; and a drag member spaced from the perforated member and elongated along a central axis parallel to a plane of the perforated member.

2. The apparatus of claim 1, in which the transducer means generates sonic waves having a component at a given frequency and the member has perforations sized to cause resonance at the given frequency.

3. The apparatus of claim 1, in which the perforations are square.

4. The apparatus of claim 1, in which the member is a screen composed of criss-crossing wires.

5. The apparatus of claim 4, in which the wires are non-conductive.

6. The apparatus of claim 4, in which the wires have a circular cross section.

7. The apparatus of claim 1, in which the tube has a cylindrical inner surface.

8. The apparatus of claim 1, in which the transducer means generates sonic waves having a component at a given frequency and the member is spaced from the outlet of the transducer means so as to cause resonance at the given frequency.

9. The apparatus of claim 1, in which the transducer means generates sonic waves having a component at a given frequency and the drag member is spaced from the perforated member so as to cause resonance at the given frequency.

10. The apparatus of claim 1, additionally comprising means for introducing liquid to the transducer means for atomization with gas introduced at the inlet.

11. The apparatus of claim 1, additionally comprising means for heating fluid outside the perforated member.

12. The apparatus of claim 11, in which the heating means is located on the drag member.

13. The apparatus of claim 1, additionally comprising means for generating an electric field between the perforated member and the drag member.

14. The apparatus of claim 1, additionally comprising means for generating an electromagnetic field in the region between the perforated member and the drag member.

15. Atomizing apparatus comprising:

vortex generating transducer means for at least partially atomizing a fluid and having a gas inlet and an outlet;

a perforated planar member spaced from the outlet of the transducer means;

a tube coupled between the outlet of the transducer means and the perforated member completely closing the space therebetween; and a cylindrical drag member spaced from the perforated member and having a central axis lying parallel to a plane of the perforated member.

* * * * *